(12) United States Patent
Dana et al.

(10) Patent No.: US 11,350,820 B2
(45) Date of Patent: *Jun. 7, 2022

(54) GRADING CORNEAL FLUORESCEIN STAINING

(71) Applicant: Massachusetts Eye and Ear Infirmary, Boston, MA (US)

(72) Inventors: Reza Dana, Newton, MA (US); Francisco L. Amparo Pulido, Cambridge, MA (US); Haobing Wang, Newton, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 16/700,575

(22) Filed: Dec. 2, 2019

(65) Prior Publication Data

US 2020/0107715 A1 Apr. 9, 2020

Related U.S. Application Data

(63) Continuation of application No. 16/016,898, filed on Jun. 25, 2018, now Pat. No. 10,492,674, which is a
(Continued)

(51) Int. Cl.
*A61B 3/00* (2006.01)
*A61B 5/103* (2006.01)
(Continued)

(52) U.S. Cl.
CPC .......... *A61B 3/0025* (2013.01); *A61B 5/0071* (2013.01); *A61B 5/1032* (2013.01);
(Continued)

(58) Field of Classification Search
CPC ... A61B 3/0025; A61B 5/0071; A61B 5/4848; A61B 5/1032; A61B 3/1025; A61B 3/14
(Continued)

(56) References Cited

U.S. PATENT DOCUMENTS

| 1,004,395 A | 9/1911 | Engebretson |
|---|---|---|
| 4,500,972 A | 2/1985 | Kuhn |

(Continued)

FOREIGN PATENT DOCUMENTS

| EP | 0859615 | 8/1998 |
|---|---|---|
| JP | 2006-512126 | 4/2006 |

(Continued)

OTHER PUBLICATIONS

CA Office Action in Canadian Appln. No. 2947295, dated Jun. 16, 2021, 5 pages.
(Continued)

*Primary Examiner* — Mohammed A Hasan
(74) *Attorney, Agent, or Firm* — Fish & Richardson P.C.

(57) ABSTRACT

The technology described in this document can be embodied in systems and computer-implemented methods for determining a score representing an amount of staining of the cornea. The methods include obtaining a digital image of the cornea stained with a tracer material, receiving a selection of a portion of the image, and processing, by a processing device, the selection to exclude areas with one or more artifacts to define an evaluation area. For each of a plurality of pixels within the evaluation area, a plurality of Cartesian color components are determined and a hue value in a polar coordinate based color space is calculated from the components. An amount of staining of the cornea is then determined as a function of the hue value. The methods also include assigning a score to the evaluation area based on the amount of staining calculated for the plurality of pixels.

20 Claims, 8 Drawing Sheets

Related U.S. Application Data continuation of application No. 15/308,184, filed as application No. PCT/US2015/028907 on May 1, 2015, now Pat. No. 10,004,395.

(60) Provisional application No. 61/988,144, filed on May 2, 2014.

(51) Int. Cl.
*A61B 5/00* (2006.01)
*A61B 3/14* (2006.01)
*A61B 3/10* (2006.01)

(52) U.S. Cl.
CPC .......... *A61B 5/4848* (2013.01); *A61B 3/1025* (2013.01); *A61B 3/14* (2013.01)

(58) Field of Classification Search
USPC ....................................................... 351/206
See application file for complete search history.

(56) References Cited

U.S. PATENT DOCUMENTS

| | | | |
|---|---|---|---|
| 4,668,979 A | 5/1987 | Jung | |
| 5,016,173 A | 5/1991 | Kenet | |
| 5,243,414 A | 9/1993 | Dalrymple | |
| 5,282,030 A | 1/1994 | Nishimura | |
| 5,291,560 A | 3/1994 | Daugman | |
| 6,337,692 B1 | 1/2002 | Ral | |
| 6,404,916 B1 | 6/2002 | De La Torre-Bueno | |
| 6,438,398 B1 | 8/2002 | Pflugfelder et al. | |
| 6,469,747 B1 | 10/2002 | Ray | |
| 6,535,632 B1 | 3/2003 | Park | |
| 6,728,401 B1 | 4/2004 | Hardeberg | |
| 6,734,899 B1 | 5/2004 | Okamoto | |
| 6,828,981 B2 | 12/2004 | Richardson | |
| 7,215,812 B1 | 5/2007 | Masaki | |
| 7,689,016 B2 | 3/2010 | Stoecker et al. | |
| 7,711,403 B2 | 5/2010 | Jay | |
| 8,009,884 B2 | 8/2011 | Chio | |
| 8,150,501 B2 | 4/2012 | Stamatas | |
| 8,244,004 B2 | 8/2012 | Free | |
| 8,295,565 B2 | 10/2012 | Gu | |
| 8,358,812 B2 | 1/2013 | Free | |
| 8,428,351 B2 | 3/2013 | Neurath et al. | |
| 8,416,258 B2 | 4/2013 | Lin | |
| 8,588,522 B2 | 11/2013 | Bhatti | |
| 8,626,268 B2 | 1/2014 | Adler | |
| 8,660,323 B2 | 2/2014 | Free | |
| 8,736,685 B1 | 5/2014 | Dorenbosch | |
| 10,492,674 B2 * | 12/2019 | Dana ................. | A61B 5/1032 |
| 2002/0176099 A1 | 11/2002 | Gil | |
| 2004/0032588 A1 | 2/2004 | Taylor | |
| 2004/0223063 A1 | 11/2004 | DeLuca | |
| 2004/0234126 A1 | 11/2004 | Hampshire | |
| 2005/0018226 A1 | 1/2005 | Chiba | |
| 2005/0105796 A1 | 5/2005 | Hong | |
| 2005/0126505 A1 | 6/2005 | Gallager | |
| 2006/0012840 A1 | 1/2006 | Fukuda | |
| 2006/0013478 A1 | 1/2006 | Ito | |
| 2006/0188157 A1 | 8/2006 | Kondo | |
| 2006/0215907 A1 | 9/2006 | Shefer | |
| 2006/0251323 A1 | 11/2006 | MacKinnon | |
| 2006/0268010 A1 | 11/2006 | Hadli | |
| 2008/0007691 A1 | 1/2008 | Mihashi | |
| 2008/0075787 A1 | 3/2008 | Hibino | |
| 2008/0170764 A1 | 7/2008 | Burns et al. | |
| 2008/0218849 A1 | 9/2008 | Uhl | |
| 2008/0226148 A1 | 9/2008 | Gu et al. | |
| 2008/0260218 A1 | 10/2008 | Smith et al. | |
| 2009/0046928 A1 | 2/2009 | Kwak et al. | |
| 2009/0059326 A1 | 3/2009 | Hong | |
| 2010/0007727 A1 | 1/2010 | Torre-Bueno | |
| 2010/0158330 A1 | 6/2010 | Guissin | |
| 2010/0158364 A1 | 6/2010 | Ma | |
| 2010/0204584 A1 | 8/2010 | Ornberg | |
| 2011/0164218 A1 | 7/2011 | Ornberg et al. | |
| 2011/0181746 A1 | 7/2011 | Free | |
| 2011/0182503 A1 | 7/2011 | Free | |
| 2011/0182507 A1 | 7/2011 | Free | |
| 2011/0182509 A1 | 7/2011 | Free | |
| 2013/0079620 A1 | 4/2013 | Kondo | |
| 2013/0195868 A1 | 8/2013 | Adelman | |
| 2013/0208981 A1 | 8/2013 | Kong | |
| 2013/0226008 A1 | 8/2013 | Dana | |
| 2013/0336557 A1 | 12/2013 | Cruzat et al. | |
| 2014/0010423 A1 | 1/2014 | Soldatitsch | |
| 2015/0036923 A1 | 2/2015 | Jia | |

FOREIGN PATENT DOCUMENTS

| | | |
|---|---|---|
| JP | 2012-517325 | 8/2012 |
| JP | 2013-544589 | 12/2013 |
| RU | 2422081 | 6/2011 |
| WO | WO 2004/058056 | 7/2004 |
| WO | WO 2009/138117 | 11/2009 |
| WO | WO 2010/071898 | 6/2010 |
| WO | WO 2012/061835 | 5/2012 |

OTHER PUBLICATIONS

Abramoff et al., "Image Processing with ImageJ," Biophotonics International (11)7:36-42 (2004).
Efron, "Clinical applications of grading scales for contact lens complications," Optician, 213:26-35 (1997).
Efron, "Grading scales," Optician 219:44-45 (2000).
Extended European Search Report in Application No. 15786468.7, dated Nov. 28, 2017, 8 pages.
Gonsales et al., "Mir tsifrovoj obrabotki. Tsifrovaya obrabotka izobrazhenij." Moskva, Tekhnosfera, p. 451, 495 (2005) (with the entire relevant chapter from the corresponding English edition).
International Search Report and the Written Opinion of the International Searching Authority issued in PCT/US2013/027132 dated Jun. 20, 2013 (7 pages).
Office Action in Australian Application No. 2015252852, dated Oct. 3, 2018, 9 pages.
Office Action in Chinese Appication No. 201580022263.5, dated Apr. 12, 2019, 7 pages (with English translation).
Office Action in Chinese Application No. 201580022263.5, dated Nov. 23, 2017, 16 pages (with English translation).
Office Action in Chinese Application No. 201580022263.5, dated Sep. 18, 2018, 9 pages (English translation).
Office Action in Japanese Application No. 2017-510456, dated Apr. 24, 2018, 10 pages (with English translation).
Office Action in Japanese Application No. 2017-510456, dated Jun. 18, 2019, 17 pages (with English translation).
Office Action in Japanese Application No. 2017-510456, dated Oct. 23, 2018, 13 pages (with English translation).
Periketi, "Gaze Estimation Using Sclera and Iris Extraction," Thesis for the degree of Master of Science in Electrical Engineering, University of Kentucky, College of Engineering, 2011, 37 pages.
Rodriguez et al., "Automated detection and enumeration of corneal superficial punctate keratitis," R & D, Ora, Inc., Andover, MA, U.S., May 8, 2013, 3 pages (Abstract).
Schulze et al., "Grading bulbar redness using cross-calibrated clinical grading scales," Invest. Ophthalmol. Vis. Sci. 52(8):5812-5817 (2011).
Schulze et al., "The Development of Validated Bulbar Redness Grading Scales," Optom Vis Sci. 84:976-983 (2007).
Tan et al., "Objective quantification of fluorescence intensity on the corneal surface using a modified slit-lamp technique," Eye and Contact Lense, 39: 3, 239-246, May 2013.
EP Office Action in European Appln. No. 15786468, dated Mar. 31, 2020, 4 pages.
Extended European Search Report in European Appln. No. 21183754.7, dated Jan. 13, 2022, 8 pages.

* cited by examiner

GRADING CORNEAL FLUORESCEIN STAINING

CROSS REFERENCE TO RELATED APPLICATIONS

This application is a continuation of U.S. patent application Ser. No. 16/016,898, filed Jun. 25, 2018, and issuing on Dec. 3, 2019 as U.S. Pat. No. 10,492,674, which is a continuation of U.S. patent application Ser. No. 15/308,184, filed Nov. 1, 2016, now U.S. Pat. No. 10,004,395, which is a 371 U.S. National application of PCT/US2015/028907, filed May 1, 2015, which claims priority to U.S. Provisional Application 61/988,144, filed on May 2, 2014. The entire contents of the foregoing are incorporated herein by reference.

FEDERALLY SPONSORED RESEARCH OR DEVELOPMENT

This invention was made with Government support under Grant No. K24 EY019098 awarded by the National Institutes of Health. The Government has certain rights in the invention.

TECHNICAL FIELD

This disclosure relates to quantitative determination of a particular color content in an image or a portion of the image.

BACKGROUND

Clinicians often grade the amount of fluorescence in corneal images of patients as a measure of corneal epithelial disease.

SUMMARY

In one aspect, this document features computer-implemented methods for determining a score representing an amount of staining of the cornea. The methods include obtaining a digital image of the cornea stained with a tracer material, receiving a selection of a portion of the image, and processing, by a processing device, the selection to exclude areas with one or more artifacts to define an evaluation area. For each of a plurality of pixels within the evaluation area, a plurality of Cartesian color components are determined and a hue value in a polar coordinate-based color space is calculated from the components. An amount of staining of the cornea is then determined as a function of the hue value. The methods also include assigning a score to the evaluation area based on the amount of staining calculated for the plurality of pixels.

In another aspect, this document features systems for determining a score representing an amount of staining of the cornea. The systems include an imaging system configured to obtain a digital image of the cornea stained with a tracer material, and a score calculator module. The score calculator module is configured to receive a selection of a portion of the image via a user interface, and process the selection to exclude areas with one or more artifacts to define an evaluation area. For each of a plurality of pixels within the evaluation area, the score calculator module determines a plurality of Cartesian color components and calculates a hue value in a polar coordinate-based color space based on the components. The score calculator module also determines an amount of staining of the cornea as a function of the hue value, and assigns a score to the evaluation area based on the amount of staining calculated for the plurality of pixels.

In another aspect, this document features computer readable storage devices that have encoded thereon computer readable instructions. The instructions, when executed by a processor, cause a processor to perform various operations. The operations include obtaining a digital image of the cornea stained with a tracer material, receiving a selection of a portion of the image, and processing the selection to exclude areas with one or more artifacts to define an evaluation area. For each of a plurality of pixels within the evaluation area, a plurality of Cartesian color components are determined and a hue value in a polar coordinate-based color space is calculated from the components. An amount of staining of the cornea is then determined as a function of the hue value. The operations also include assigning a score to the evaluation area based on the amount of staining calculated for the plurality of pixels.

In another aspect, this document features methods of determining severity of an eye condition. The methods include determining a score for a cornea of a subject using the method described above. The determined score can indicate the severity of the condition.

In another aspect, this document features methods of monitoring efficacy of a treatment for a condition of the cornea of a subject. The methods include determining a first score for the cornea of the subject, administering one or more treatments to the eye of the subject, and determining a second score for the cornea of the subject. The first and second scores can be determined by the methods described herein. The methods also include comparing the first and second scores. Changes in the scores can be used as indications of whether or not the treatment is effective. For example, a decrease in a score can indicate that the treatment was effective, and no change or an increase in a score can indicate that the treatment was ineffective.

In another aspect, this document features methods of monitoring progression of a condition of the cornea of a subject. The methods include determining a first score for the cornea, and determining a second score for the cornea. The first and second scores can be determined by the methods described herein. The methods also include comparing the first and second scores. Changes in the scores can be used as indications of whether or not the treatment is effective. For example, wherein a decrease from the first score to the second score can indicate that the condition is improving, no change between the first and second scores can indicate that the condition is stable, and an increase from the first score to the second score can indicate that the condition is worsening.

Implementations of the above aspects can include one or more of the following.

The selection can be received via an adjustable control overlaid on the digital image of the cornea. Processing the selection can include dividing the selection into a plurality of zones, analyzing each of the zones to detect a presence of the one or more artifacts, and modifying the selection to exclude zones in which the presence of the one or more artifacts are detected to define the evaluation area. The one or more artifacts can include one of a specular reflection and a confocal reflection. The specular or confocal reflection can be detected using a flooding algorithm. Determining the amount of staining can include mapping an angle corresponding to the hue value to a scalar value within a predetermined range, and determining the amount of staining as a product of the scalar value and at least one component of the polar coordinate based color space that is different from the hue. A parabolic curve can be used in mapping the angle to the scalar value within the predetermined range. The tracer material can be a fluorophore such as fluorescein. The digital image can be acquired in the presence of blue cobalt light. The score can indicate a degree of greenness of the image of the cornea. The Cartesian color space can be the Red-Green-Blue (RGB) color space. The polar coordinate-based color space can be the Hue-Saturation-Value (HSV) color space. The score and an association of the score with the digital image can be stored on a storage device. The digital images can represent corneas afflicted with a corneal epithelial disease, dry-eye syndrome, ocular graft-versus-host disease, and Sjogren's syndrome. The score being above a reference score can indicate that the subject has a disease.

Particular implementations may realize none, one, or more of the following advantages. Corneal images taken using different imaging systems can be evaluated based on a standardized scale and quantitatively compared with one another. This can allow for repeatability, consistency, and accuracy because the corneal images are not scored based on subjective judgment of a human observer. The scoring system can be made sensitive to detecting small changes in corneal fluorescein staining that might not be detectable by a human observer. The methods and systems described herein thus provide an objective technique that can be used, e.g., to diagnose and to monitor response to therapy, using a computer based analysis.

Unless otherwise defined, all technical and scientific terms used herein have the same meaning as commonly understood by one of ordinary skill in the art. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages will be apparent from the following detailed description and figures, and from the claims.

DETAILED DESCRIPTION

Figure 1:
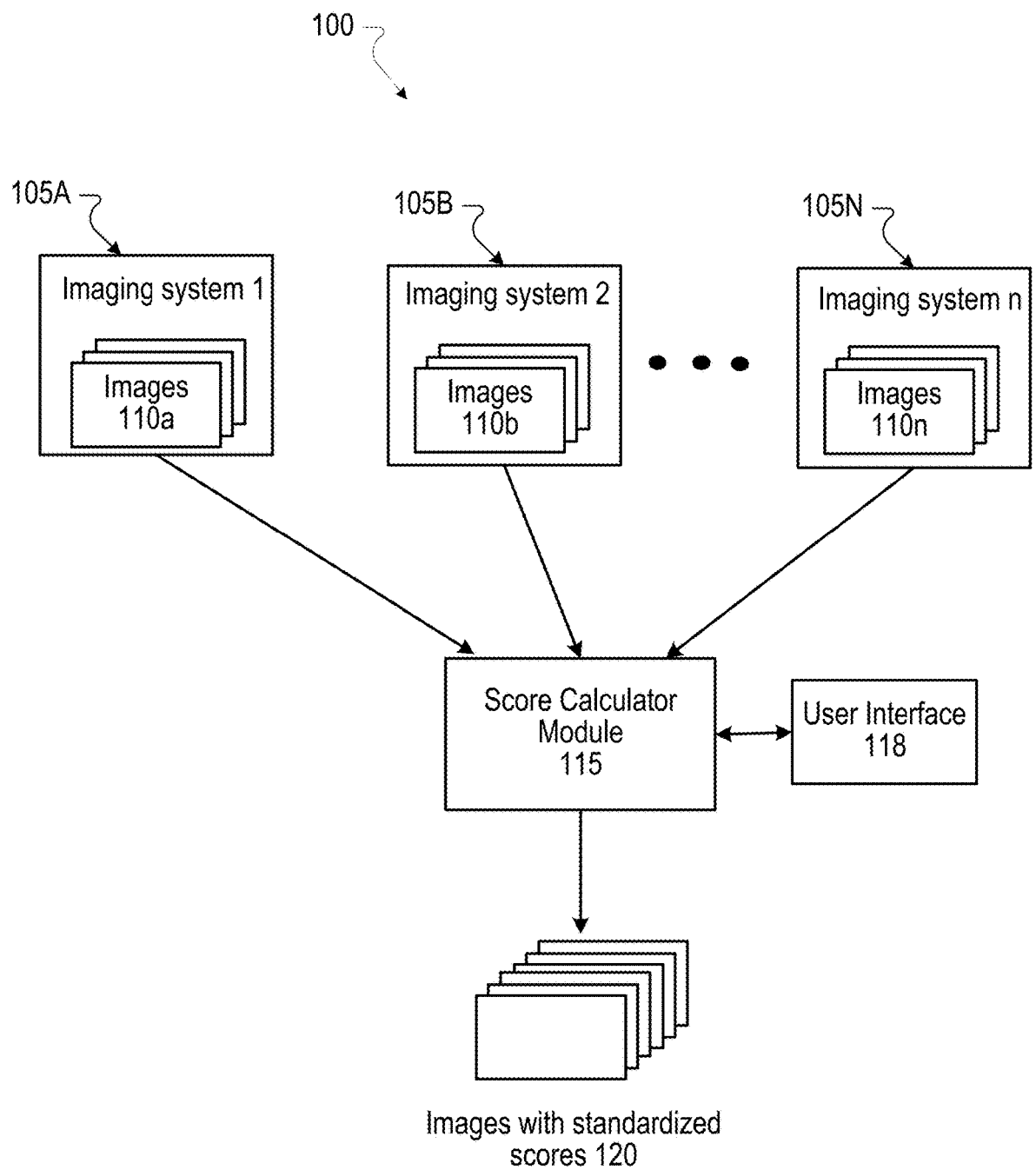
FIG. 1 is a block diagram of an example of a system for calculating scores for corneal images acquired through different imaging systems.

Presented here are techniques that can be used to assess and quantify conditions such as corneal epitheliopathy, which as used in this document, broadly refers to afflictions or diseases of the epithelium. Corneal epitheliopathy manifests as focal punctate areas with a tendency to converge. These areas can be identified from digital images acquired after staining the areas with a tracer material such as fluorescein. The areas with epitheliopathy capture fluorescein dye instilled onto the ocular surface and are manifested as focal punctuate areas. During a clinical exam, the clinician directs a blue cobalt light towards the cornea, thus stimulating the captured dye and producing a green fluorescent signal. Grading the amount of fluorescence due to fluorescein is known as Corneal Fluorescein Staining (CFS) grading, and can be used to evaluate diseases that affect the ocular surface. Examples of such diseases include corneal epitheliopathy, dry eye, ocular graft-versus-host-disease, Sjogren's syndrome, and corneal ulcers secondary to various infections (e.g., herpes virus, bacterial).

Ophthalmologists often grade or quantify the amount of fluorescence in corneal images based on a visual inspection. In some cases, the images are visually compared to reference drawings or photographs to bin them into various categories. For example, the National Eye Institute (NEI) provides a corneal fluorescein scoring system where the corneal surface is divided in five regions. Each region is graded with a score between one and three points based on the level of fluorescence in the region. The scores from the five regions are added, resulting in a maximum of fifteen points for the most affected corneas. The threshold for a three-point score in a given region is relatively low and patients with moderate conditions often receive a three point score for a given region. In addition, even if a highly affected area experiences moderate improvement, the area may receive the same score that it did prior to the improvement. Therefore, the system may not be sensitive enough to detect changes in moderate to severe conditions.

The above mentioned methods can therefore be subjective and prone to errors. For example, the same image can be graded differently by two different clinicians, or even when the same clinician grades the image at two different times. In addition, human observers may also not be able to detect small changes, rendering such visual grading coarse-grained and prone to inaccuracies.

The technology described in this document allows computer-based analysis of digital images of the cornea such that images across different imaging systems, conditions and time can be evaluated based on a standardized score assigned to each of the images. The techniques described in this document facilitate quantifying the fluorescence in corneal images, and objectively determining the condition of affected areas on the corneal surface. By quantifying the intensity of the fluorescent signal, the techniques allow for distinguishing between severe epithelial defects that tend to capture more fluorescein and therefore emanate stronger signals, from mild to moderate dry eye corneal epitheliopathy that is diffuse and emanate weaker signals. Therefore, locations with severe damage can be identified even if the location is not spread over a large area of the cornea.

FIG. 1 shows a block diagram of an example of a system 100 for calculating scores for corneal images acquired through different imaging systems. The system 100 includes one or more imaging systems 105A, 105B, . . . , 105N (105, in general). The imaging systems 105A, 105B, . . . , 105N are used to acquire images sets 110a, 110b, . . . , 110n, respectively (110, in general). The imaging systems 105 can be different or substantially similar to one another. For example, the imaging system 105A can be a slit-lamp camera and the imaging system 105B can be a standard digital photography camera. In another example, the imaging systems 105A, 105B, . . . , 105N can all be slit-lamp cameras of different makes, models or have imaging parameters that are different from one another. The corresponding image sets 110 acquired by the different imaging systems 105 can therefore vary significantly from one another. For example, the images across the different imaging systems 105 can vary from one another in resolution, white balance, lighting characteristics or other image parameters. In some implementations, for corneal imaging, the imaging systems 105 can be configured to obtain the images in the presence of light that excites the fluorophore used as the tracer material. For example, in case of Corneal Fluorescein Staining imaging (in which fluorescein is used), the images can be acquired by the imaging systems 105 in the presence of blue cobalt light. In such cases, images taken by different imaging systems cannot be reliably compared to one another based simply on visual inspection by a human observer. For example, if two corneal images taken by different imaging systems are compared by a human observer, the perceived difference in the imaged fluorescence may be due to inherent differences in the imaging hardware and/or software.

The corneal image sets 110 can be obtained, for example, by administering a tracer material to the eye and imaging the eye under particular lighting conditions. For example, the tracer material can include a fluorophore, i.e., a fluorescent chemical compound that can re-emit light upon light excitation. The fluorophore can include organic compounds having aromatic groups, or plane/cyclic molecules with several a bonds.

The fluorophore used in staining the cornea often includes fluorescein. Fluorescein, a synthetic organic compound, is soluble in water and alcohol at least to some degree. Fluorescein is widely used as a tracer material because of having desirable fluorescence properties. In some implementations, fluorescein sodium, a sodium salt of fluorescein, can be used as a tracer material in the diagnosis of corneal abrasions, corneal ulcers and herpetic corneal infections. In some implementations, fluorescein or one of its derivatives can also be used in contact lens fitting to evaluate the tear layer under the lens.

In some implementations, the corneal images 110 acquired by the same imaging system 105 can vary from one another. For example, if the images are taken some time apart, variability due to, for example, parameter drift, or different lighting conditions can contribute to the variability of the images. In some implementations, the techniques described herein can be used to analyze corneal images from different clinical centers and patients, to compare them quantitatively. The techniques can also be used, for example, to optimize CFS evaluation in clinical trials. The manual grading systems typically used in controlled trials may lack adequate resolution for detecting changes (improvement or worsening) in corneal staining after a treatment is administered. As a result, advanced clinical trials for drugs often fail because of a lack of clear determination of disease endpoint achievements. The techniques described herein can be used to evaluate corneal images objectively, thereby allowing for accurate assessments of changes attributable to a drug or treatment regimen.

The system 100 includes a score calculator module 115 that can be used to determine or assign a score to the corneal images 110 or to portions thereof. The score calculator module 115 can be implemented on a computing device and configured to account for variability that exists in images acquired using one or more imaging systems 105. In some implementations, the score calculator module 115 can be implemented using a general purpose computer such as a desktop or laptop computer or a mobile device that is capable of executing one or more software programs. In some implementations, the score calculator module 115 is configured to execute one or more image processing application programs such as ImageJ, developed at the National Institutes of Health. In some implementations, the score calculator module may be implemented as a plug-in (e.g., a Java-based plug-in) for Image J or other image analysis tool.

In some implementations, the score calculator module 115 includes a user interface 118 that is configured to accept user input as well as provide score outputs to a user. In some implementations, a user can interact with the score calculator module 115 through the user interface 118. In some implementations, the score user interface 118 can include an adjustable control over overlaid on an image. For example, the user interface 118 can include a circle (or another shape) that is overlaid on a corneal image. The user may be allowed to adjust the circle to fit the corneal size. The user interface 118 therefore provides the flexibility of a user choosing the corneal shape to facilitate a more accurate score calculation.

In some implementations, the score calculator module 115 can be configured to process the corneal image to exclude areas that include undesirable imaging artifacts, which may lead to inaccuracies in the calculated score. Examples of such artifacts include specular reflections and confocal reflections. A specular reflection in a corneal image occurs due to reflection of light from the surface of the eye, and is manifested as one or more spots of high intensity within the corneal image, and do not represent the true colors of the corneal image.

The score calculator module 115 can employ various processes to detect the areas that include the undesirable imaging artifacts. For example, the areas with specular reflections can be detected using a flooding algorithm. For example, pixels that satisfy threshold conditions on the values of one or more of the R, GC and B components can be detected, and the pixel value can be set at an initial high value. A contiguous area can then be selected such that the pixel values within the contiguous area are within a certain tolerance range above or below the initial value. The area can then be flagged (for example, by setting the color of the pixels as red) as specular reflections. In some implementations, the process can be repeated over the entire image to detect specular reflections or other artifacts.

In some implementations, a grid can be overlaid on the corneal image to divide the corneal image into a plurality of areas. For example, the NEI corneal fluorescein staining scoring system grid, which divides the corneal area into five zones or areas can be used. Other types of grids with more or less number of zones can also be used. The areas that are determined to include the undesirable artifacts can then be excluded from subsequent calculations to determine the score for the corneal image. An evaluation area can be defined upon exclusion of the areas with the undesirable artifacts. In some implementations, where the corneal image does not include any undesirable artifact, the entire image of the cornea may be included within the evaluation area.

In some implementations, the score calculator module 115 calculates a score for the evaluation area in accordance with one or more image analysis techniques described below. In some implementations, the score for a given corneal image is determined as a sum of the scores for the individual zones, except the zones that are excluded because of having one or more artifacts. In some implementations, only the particular pixels that represent artifacts are excluded from the score calculation for the entire corneal image. The image analysis techniques can include determining color information from pixels of the evaluation area. In general, the score calculator module 115 assigns scores to the corneal images 110 or portions thereof and outputs an image set 120 in which each image is associated with a standardized score. For example, the image set 120 can include one or more corneal images 110 that are assigned a corresponding score based on the amount of fluorescein staining detected in the image. The images from the set 120 and an association with the respective scores can be stored in a storage device.

The methods and systems described herein process digital images or portions thereof based on their color properties. Color properties can be described, for example, using color spaces that represent colors as tuples of numbers, typically as three or four values or color components. Examples of color spaces include RGB, CMY, CMYK, YIQ, YUV, YCrCb, HSV, HSI, IHC and HSL color spaces. In general, color spaces can be broadly classified into Cartesian and polar coordinate based color spaces. An understanding of such color spaces is important in the methods and systems described herein and are therefore described next with reference to FIGS. 2A-2D.

Figure 2A:
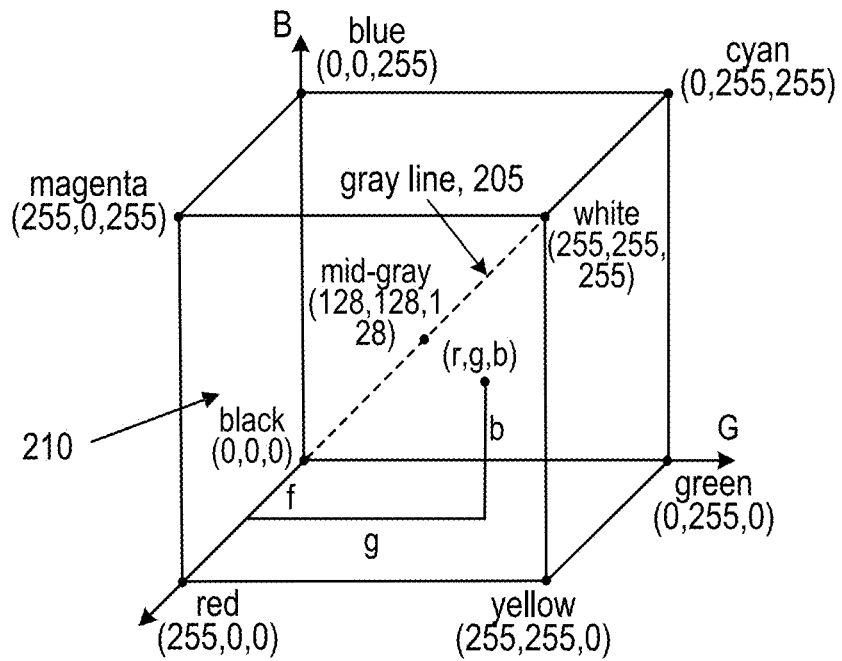
FIG. 2A depicts a Cartesian color space.

Referring now to FIG. 2A, an RGB color space is shown as an example of a Cartesian color space. In this color space, a color is represented in a three dimensional Cartesian space composed on three axes red, green and blue. The RGB color space is an additive color model in which red, green, and blue colors are added together in various ways to reproduce a broad array of colors. The RGB color space is typically used for sensing, representation, and display of images in electronic systems, such as televisions, digital cameras, computers and handheld mobile devices. In the example shown in FIG. 2A, different colors are encoded using three 8-bit unsigned integers (0 through 255) representing the intensities of red, green, and blue. This representation is the current mainstream standard representation in image file formats such as JPEG or TIFF. Such encoding of the RGB space results in more than 16 million different possible colors. As shown in FIG. 2A, the colors at the vertices of the RGB color space may be represented as the following points: (0, 0, 0) is black, (255, 255, 255) is white, (255, 0, 0) is red, (0, 255, 0) is green, (0, 0, 255) is blue, (255, 255, 0) is yellow, (0, 255, 255) is cyan and (255, 0, 255) is magenta. Any point in the volume bounded by these vertices represents a mixed color that can be broken down into red, green and blue components and represented in the RGB space as a point (r, g, b). Further, lines and planes may also be defined in the RGB color space. For example, the line connecting pure black (0, 0, 0) and pure white (255, 255, 255) may be defined as a gray line 205. Other examples of Cartesian color spaces include the YIQ, YUV and YCbCr spaces.

The Cartesian color spaces, while ideal for describing colors in digital formats, are not well suited for describing colors that are practical for human interpretation. For example, human beings do not perceive a color in terms of its component primary colors. Rather, humans usually describe a color by its hue, saturation and brightness or intensity. Hue is an attribute that describes what a color actually is (for example, red, yellow, orange, and cyan), whereas saturation is a measure that describes to what extent the color is diluted by white light. Brightness is a descriptor that embodies the achromatic notion of intensity and is an important factor in describing color perception. Color spaces based on these attributes of colors are ideal for algorithms related to human perception of color, such as described herein. The IHC (Intensity, Hue, Chroma) color space described with respect to FIG. 2B is an example of such a color space.

Figure 2B:
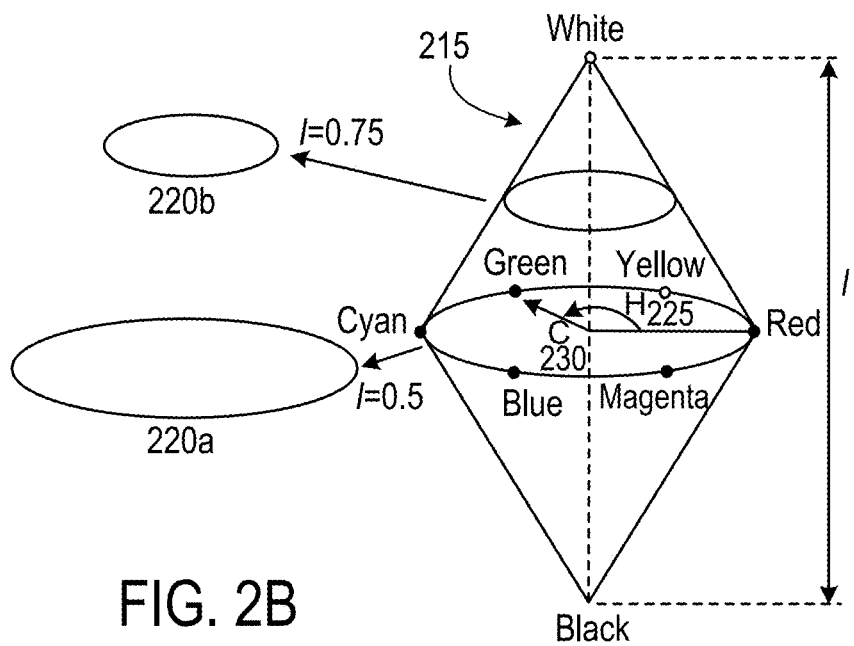
FIGS. 2B-2D depicts polar coordinate based color spaces.

Referring to FIG. 2B, the IHC color space includes of a vertical intensity axis 215 and loci 220a, 220b (220 in general) of color points that lie on planes perpendicular to the axis. The hue (H) 225 of a color point within a locus plane (220a for example) is represented by an angle with respect to a reference point while a chroma (C) 230 is represented as a linear distance of the point from the point of intersection of the locus plane 220a with the intensity axis 215. Even though, the example in FIG. 2B shows the loci 220 to be circular in shape, other polygonal shapes, such as triangles, pentagons, hexagons etc., may be used to represent the loci. The area of the loci 220 is a function of the intensity. In other words, the range of chroma is also dependent on the intensity. For example, at zero intensity (i.e., I=0), all colors have zero chroma value and converge to black. Similarly, for the maximum intensity (e.g., I=1), all colors have zero chroma value and converge to white. Within this range, the area of the loci 220 (or the range of chroma values) may increase, for example from I=0 to I=0.5 and then decrease again from I=0.5 to I=1. FIG. 2B shows the locus 220b corresponding to intensity I=0.75. For a given locus plane 220, the hue of a color point is determined by an angle from a reference point. In this example, red designates the reference point, i.e. zero hue, and the hue increases in a counterclockwise direction from the reference point. Other polar coordinate based color spaces, such as the HSL (Hue, Saturation, Lightness) and HSV (Hue, Saturation, Value) color spaces, also follow similar principles with hue being represented as an angle in an polar coordinate based coordinate system.

Figure 2C:
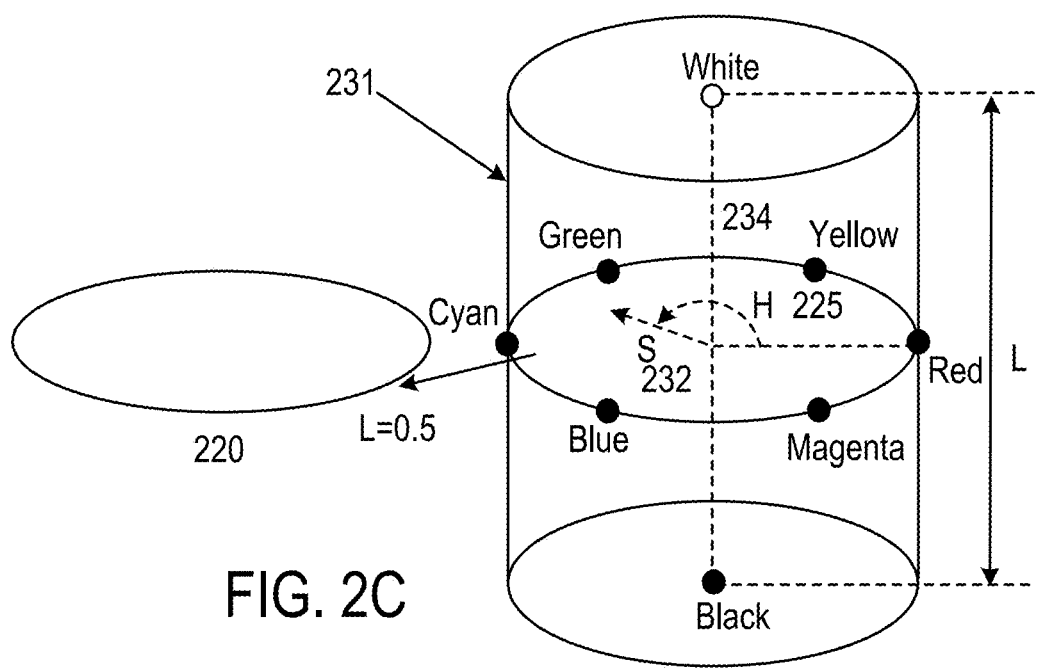

Referring now to FIG. 2C, a HSL color space also includes of a vertical axis and loci 220 of color points that lie on planes perpendicular to the axis. In this color space, the vertical axis represents lightness (L) 234. The HSL color space is also referred to HLS or HSI with I standing for intensity. The HSL color space represents colors as points in a cylinder 231 (called a color solid) whose central axis 234 ranges from black at the bottom to white at the top, with colors distributed between these two extremities. The angle around the axis corresponds to the hue 225, the distance of a point on a given locus 220 from the axis corresponds to the saturation 232, and the distance along the axis 234 corresponds to lightness or intensity. Unlike the chroma 230 in the IHC color space (FIG. 2A), the range of the saturation 232 is not a function of the lightness or intensity.

Figure 2D:
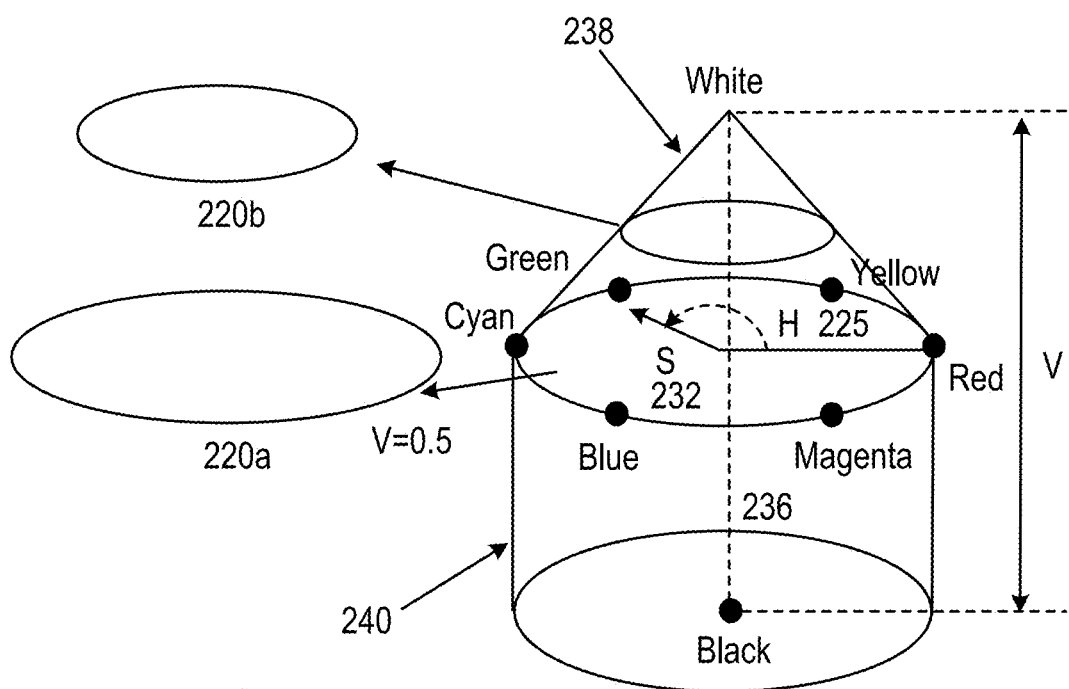

Referring now to FIG. 2D, an example of a HSV color space represents colors via an inverted color cone 238 on a cylinder 240. Other representations of the HSV color space are also possible. In this example, the HSV color space includes a common vertical axis 236 for the cone 238 and the cylinder 240. The central axis 236 ranges from black at the bottom to white at the top, with colors represented in loci 220 distributed between these two extremities. The angle around the axis corresponds to the hue 225, the distance of a point on a given locus 220 from the axis corresponds to the saturation 232, and the distance along the axis 234 corresponds to the value V. The value can be scaled to be between 0 and 1. In this color space, the saturation 232 is a function of the value V when V is between 0.5 and 1. For example, when V=1, all colors converge to pure white. When V is between 0 and 0.5, the range of the saturation is constant and not a function of the value, as shown in FIG. 2D.

In some implementations, hue information from digital images are used in the methods and systems described herein. In some implementations, color information corresponding to pixels in a digital image are converted to a polar coordinate based color space in determining a score that represents a particular color content. For example, in determining a redness value for a portion of a digital eye image, the color information from the pixels can be converted from the RGB color space to the HSV color space and the hue information can be used in calculating the redness score of the portion. As described with respect to FIG. 2B, in general, hue is an attribute of polar coordinate based color spaces while most digital images are represented using Cartesian coordinate systems such as the RGB color model. The RGB color information may be transformed into a polar coordinate based color space such as the HSI color space. For example, the hue may be calculated as:

$$H = \begin{cases} \theta & B \leq G \\ 360 - \theta, & B > G \end{cases}$$

$$\text{where } \theta = \cos^{-1}\left\{\frac{\frac{1}{2}[(R-G)+(R-B)]}{[(R-G)^2+(R-B)(G-B)]^{1/2}}\right\}$$

The saturation component is given by:

$$S = 1 - \frac{3}{(R+G+B)}[\min(R, G, B)]$$

The intensity of the component is given by:

$$I = \frac{1}{3}(R+G+B)$$

In some implementations, the RGB color information can be transformed into the HSV color space using the following equations. For example, the value component V can be calculated as:

$$V = \max(R, G, B)$$

The saturation component S can be calculated as:

$$S = \frac{\text{delta}}{\max(R, G, B)} \begin{cases} \text{if} & \max(R, G, B) \neq 0 \\ \text{else} & S = 0 \end{cases}$$

wherein $$\text{delta} = \max(R, G, B) - \min(R, G, B)$$

The hue component H is given by:

$$\begin{cases} \text{delta} \neq 0 \begin{cases} H = \frac{60 \times \left(\frac{G-B}{\text{delta}}\right) + 360}{360} & \{\text{if } \max(R, G, B) = R\} \\ H = \frac{60 \times \left(\frac{B-R}{\text{delta}}\right) + 360}{360} & \{\text{if } \max(R, G, B) = G\} \\ H = \frac{60 \times \left(\frac{R-G}{\text{delta}}\right) + 360}{360} & \{\text{otherwise}\} \end{cases} \\ \text{delta} = 0 \quad \{H = 0\} \end{cases}$$

Figure 3A:
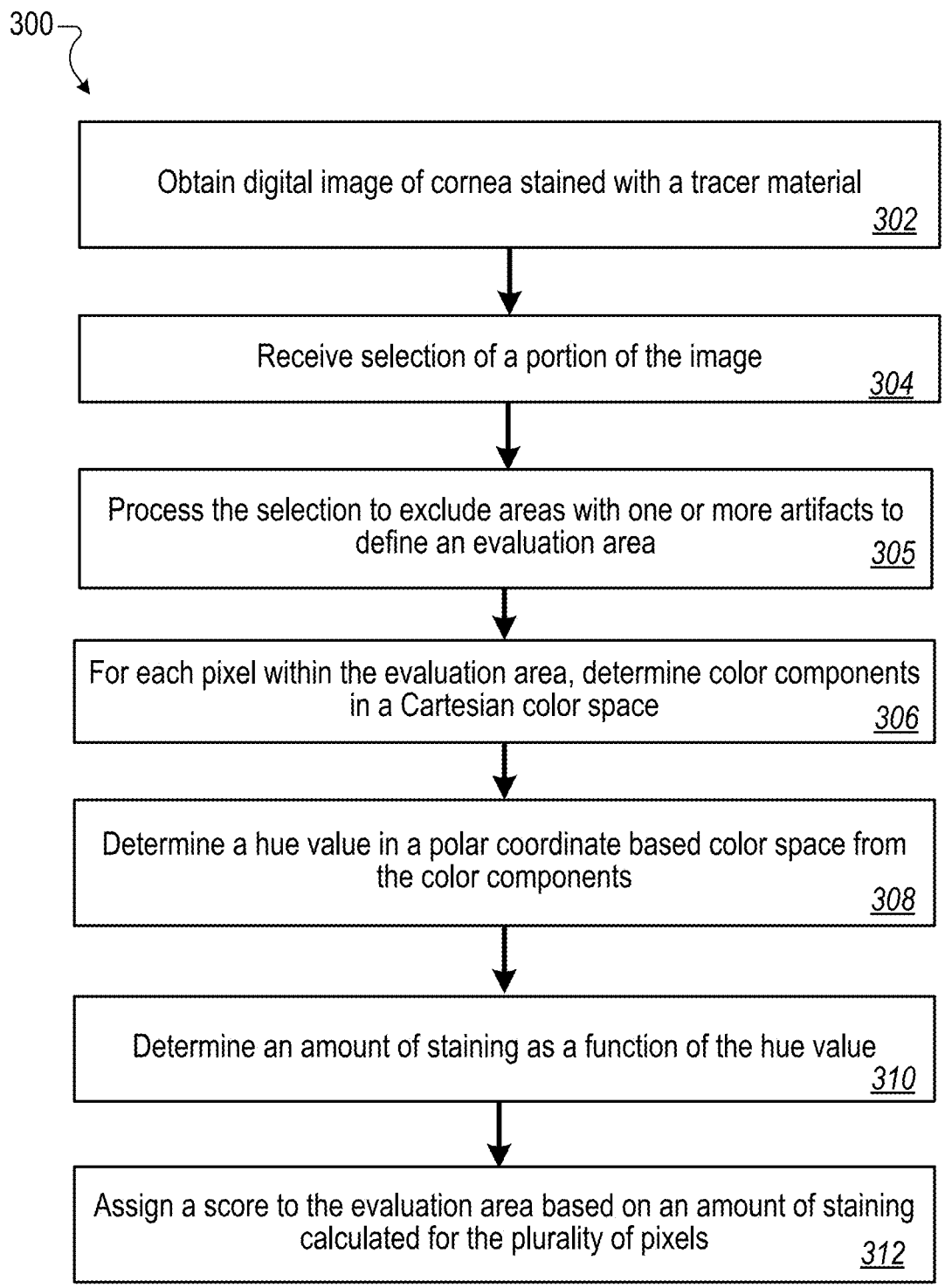
FIG. 3A is a flowchart representing an example sequence of operations for determining a score for digital image of the cornea.

Referring now to FIG. 3, a flowchart 300 represents an example sequence of operations for determining a score of a digital image. In some implementations one or more of the operations can be executed at the score calculator module 115 described with reference to FIG. 1.

The operations include obtaining a digital image of the cornea stained with a tracer material (302). The tracer material can include a fluorophore such as fluorescein. The digital image can be obtained from an imaging system substantially similar to the imaging system 105 described with reference to FIG. 1. In some implementations, the digital image can be acquired in the presence of light that excites the fluorophore used as the tracer material. For example, in case of CFS imaging (in which fluorescein is used), the digital image can be acquired in the presence of blue cobalt light. In some implementations, the digital image can be obtained substantially directly from the imaging system. In some implementations, obtaining the digital image can include retrieving the digital image from a storage device.

Operations can also include receiving a selection of a portion of the image (304). The selection can be received, for example, through a user interface substantially similar to the user interface 118 described with reference to FIG. 1. The selection operation can allow a user, for example via an adjustable control overlaid on the digital image of the cornea, to accurately select a region of interest from the cornea. This can be done, for example, by providing a circle (or another shape) that is overlaid on the corneal image. The user may be allowed to adjust the circle (or any other shape that is provided) to accurately select a region of interest within the cornea. The region of interest can also include the entire cornea. The interactive selection process also allows for repeatability to evaluate a substantially same area in different images.

Operations also include processing the selection to automatically exclude areas with one or more artifacts to define an evaluation area (305). The artifacts can include, for example, specular reflection and confocal reflection. The artifacts such as specular or confocal reflections can be detected, for example, using a flooding algorithm, and the areas in which they are detected can be excluded from the evaluation area to improve the accuracy of the score. In some implementations, the artifacts can also be determined using a threshold for pixel intensities. The threshold can be set, for example, by a clinician to avoid artifacts in the corneal images. In some implementations, the threshold is set such that pixel intensities that satisfy a threshold condition are flagged as artifacts and the corresponding zones or regions are excluded from the evaluation area.

For each of a plurality of pixels within the evaluation area, the Cartesian color components are determined (306). For example, if the digital image is represented using the RGB color space, the red, green and blue components corresponding to the pixel value are determined. In some implementations, the color components can be associated with another Cartesian color space such as the CMY color space. In some implementations, the plurality of pixels includes all pixels in the evaluation area. In some implementations, only a subset of the pixels within the evaluation is considered in calculating the score.

Operations further include determining a hue value from the Cartesian color components (308). As described above with reference to FIGS. 2B-2D, hue is a component of a polar coordinate based color space and therefore determining the hue value can include converting the Cartesian color components to a polar coordinate based color space. The polar coordinate based color space can include, for example, the HSV color space. Converting the Cartesian color components to a polar co-ordinate based color space can be done, for example, using the conversions described above with reference to FIGS. 2A-2D. The hue value can be described in terms of an angle also as described with reference to FIGS. 2B-2D.

Figure 3B:
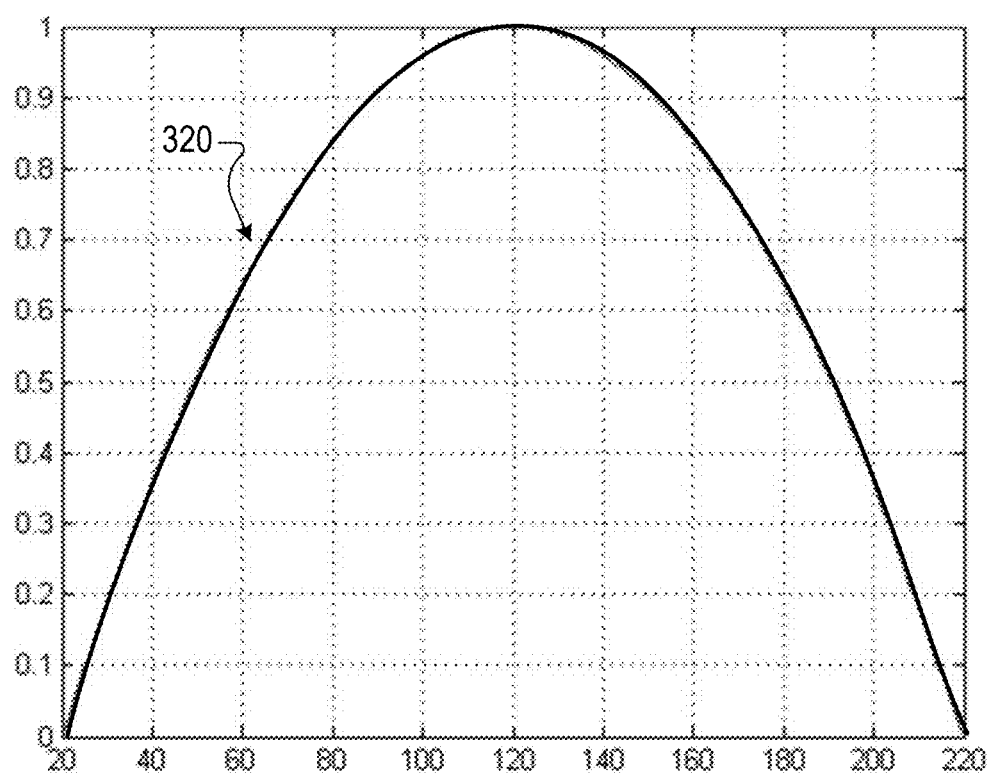
FIG. 3B is an example of a curve used in an operation depicted in FIG. 3A.

Operations also include determining an amount of staining for each of the plurality of pixels (310). In some implementations, determining the amount of staining includes mapping an angle corresponding to the hue value (e.g., between 0 and 360°) to a scalar value within a predetermined range (e.g., 0 and 1). For example, in determining amount of fluorescein staining, the hue values corresponding to a greenness of the image may lie within 20° and 220°. In some implementations, the angle values can be mapped to a scalar range between, for example, 0 and 1. The mapping may be linear or non-linear. FIG. 3B shows an example of using a non-linear curve such as a parabola 320 to map hue values between 20° and 220° (represented along the x-axis) to a scalar range between 0 and 1 (represented along the y-axis). In some cases, a linear function may also be used. For example, in determining an amount of staining in CFS images, a linear function may work better between 200° and 220° to avoid any confusion between the aqua or cobalt blue (color of the light source utilized to excite fluorescein) and the green (color of actual fluorescence representing epithelial defects). Other angle ranges can be used for other fluorophores. In some implementations, the angle range that is mapped on to the scalar value can be selected based on a location of a color in the hue circle. For example, in measuring an amount of staining in images related to CFS, an angle range corresponding to observed shades of green (or green-yellow) can be selected.

In some implementations, the scalar value itself can be used to represent the amount of staining. In some implementations, the value representing the amount of staining (also referred to as staining intensity) for a given pixel is determined as a product of the scalar value and one or more components of the polar coordinate based color space. In some implementations, when the HSV color space is used for measuring fluorescein staining, the staining intensity can be referred to as greenness, and determined as a product of the scalar value with one or both of the S and V components. For example, the greenness of a pixel can be computed as:

$$greenness = H \times S \times V.$$

If each of the H, S, and V components are normalized to be in the range [0,1], the greenness score is also within the range of [0, 1]. In such cases, a score of zero implies that there is no greenness in the particular pixel, whereas a score of one implies that the pixel is completely green. In some implementations, a threshold may be applied to determine whether a particular pixel represents staining. For example, if a threshold of 0.018 is applied, a given pixel is determined to represent staining only if the greenness value is higher than 0.018. In some implementations, the threshold may be defined by a clinician (e.g., an ophthalmologist) or empirically determined using a set of control images.

In some implementations, an upper limit may also be defined for the staining intensity (e.g., greenness). In such cases, the staining intensity corresponding to a perceived high amount of staining can be used as the upper limit. For example, if the greenness corresponding to such perceived high amount of staining is 0.4, any greenness score equal to or higher than 0.4 can be assigned the maximum possible value. Any values equal to or greater than 0.4 can then be assigned a value of 1, i.e., the maximum possible value. In some implementations, greenness values in the range [0, 1] can be remapped to a wider range such as [0, 100].

Operations further include assigning a score to the evaluation area (312). In some implementations, the score is determined as an average of the staining intensities corresponding to the plurality of pixels in the evaluation area. In some implementations, other measures of central tendency such as weighted average, median value or mode can also be used in determining the score. In some implementations, the score can be scaled to a value within a predetermined range (e.g. [0, 100]) before being assigned to an evaluation area. The predetermined range can be chosen based on, for example, the type of image or application. In some implementations, the scaling can be such that the highest determined score maps on to the upper end of the predetermined range (100, in this example) and the lowest determined score maps on to the lower end of the predetermined range (0, in this example). The score is then mapped on to an appropriate value within the predetermined range. In some implementations, the predetermined range can be fixed based on predetermined high and low color values. In such cases, color values higher than the highest predetermined value are mapped on to the upper end of the range and color values lower than the lowest predetermined value are mapped on to the lower end of the range. In some implementations, the determined score is saved in a storage device along with an association that links the score with the corresponding image.

In some implementations, assigning the score to the evaluation area also includes generating a table of percentage of a staining area. In some implementations, a threshold for the staining intensity can be used to determine whether or not a particular pixel is part of a staining area. For example, a given zone or area of the cornea is determined to be 20% stained if 20% pixels in the zone or area have staining intensities that exceed the threshold. The threshold can be clinician-defined or empirically determined.

The staining in corneal images can therefore be represented both in terms of stained area and staining intensity. For example, if a given zone has a low average staining intensity, but a high percentage of staining area, the zone may be determined to have widespread superficial epithelial damage. In another example if a given zone has a low percentage of staining, yet pockets of high staining intensities, the zone may be determined to have localized but deep lesions.

In some implementations, the obtained digital image may be subjected to one or more pre-processing operations prior to calculating the score. The pre-processing operations can include, for example, noise removal or white balancing.

Figure 4:
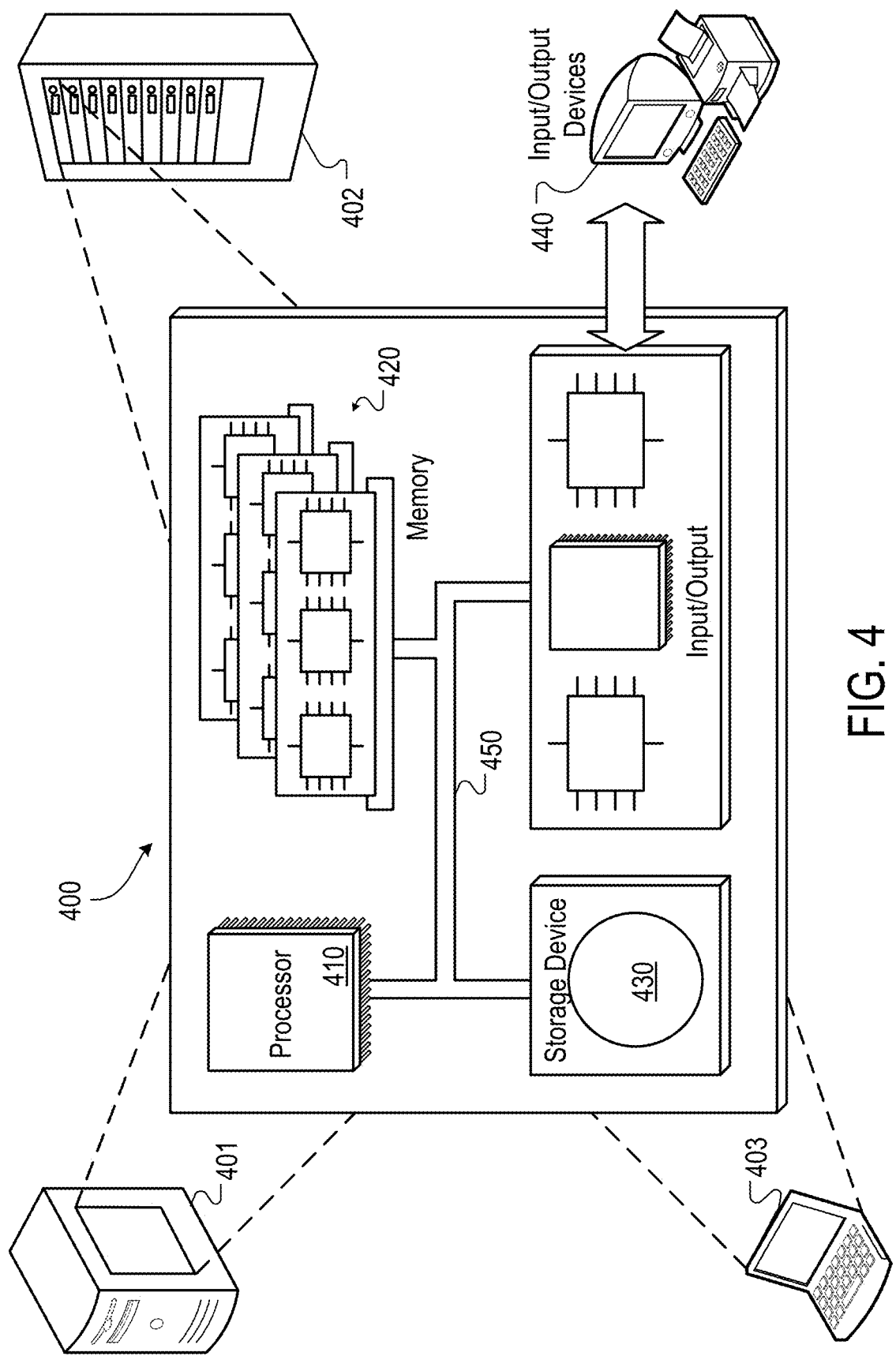
FIG. 4 is a block diagram of an example of a computing system.

FIG. 4 is a schematic diagram of a computer system 400. The system 400 can be used for the operations described with reference to the flowcharts in FIG. 3A. The system 400 can be incorporated in various computing devices such as a desktop computer 401, server 402, and/or a mobile device 403 such as a laptop computer, mobile phone, tablet computer or electronic reader device. The system 400 includes a processor 410, a memory 420, a computer-readable storage device 430 (which may also be referred to as a non-transitory computer readable storage medium), and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In some implementations, the memory 420 is a computer-readable storage medium. The memory 420 can include volatile memory and/or non-volatile memory. The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In some implementations, the input/output device 440 includes a keyboard and/or pointing device. In some implementations, the input/output device 440 includes a display unit for displaying graphical user interfaces. In some implementations the input/output device can be configured to accept verbal (e.g. spoken) inputs.

The features described can be implemented in digital electronic circuitry, or in computer hardware, firmware, or in combinations of these. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display) monitor, eInk display or another type of display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 410 carries out instructions related to a computer program. The processor 410 may include hardware such as logic gates, adders, multipliers and counters. The processor 410 may further include a separate arithmetic logic unit (ALU) that performs arithmetic and logical operations.

The methods and systems described herein can be used in a number of clinical applications. For example, a score can be used to determine the severity of a disorder associated with the presence of the staining intensity. Taking corneal epitheliopathy as an example, the presence of which is associated with a number of conditions (including, but not limited to dry eye syndrome, graft-versus-host disease, Sjogren's syndrome, allergies, corneal infections, etc.), a higher score determined by a method described herein can be associated with greater severity of the condition. A lower score can indicate that the condition is less severe.

The methods can also be used to monitor progression or treatment of a condition. For example, a first score and/or percentage area are determined at a first time point, e.g., before or during administration of a treatment for the condition associated with the presence of the staining intensity, and a second score is determined at a later time. Again taking corneal epitheliopathy as an example, a first score and/or percentage area are determined at a first time point, e.g., before or during treatment, and a second score and/or percentage area are determined at a later time point. The two scores can then be compared, and an increase in the score can indicate progression (i.e., worsening) of the condition or a lack of efficacy of the treatment; no change can indicate that any treatment has at best stopped progression (in a progressive disorder), or has been ineffective; and a decrease in the score can indicate that the treatment has been effective. An increase in the percentage area can indicate that the condition is spreading, whereas a decrease can indicate that the spread area is reducing.

EXAMPLES

The methods and systems described herein are further described using the following examples (with reference to FIG. 5A-5D), which do not limit the scope of the claims. FIGS. 5A-5D illustrate score and area determination for fluorescein staining. The images were obtained from patients with dry eye disease. A Haag-Streit BQ 900 IM imaging system was used to acquire the images. Fifty images from patients with dry eye disease were analyzed, and a strong correlation was found between the scores of NEI corneal fluorescein staining and the scores computed using the technique described above. A metric known as the Spearman's coefficient of correlation (R) was computed based on the data. The coefficient of correlation is a metric that represents the degree of co-variation between two variables, and indicates the degree to which two variable's movements are associated. The value of R varies between −1.0 and 1.0. An R value of 1.0 indicates that there is perfect correlation between the scores of both variables. An R value of −1.0 indicates perfect correlation in the magnitude of the scores of both variables but in the opposite direction. On the other hand, an R value of 0 indicates that there is no correlation between the scores of the two variables. The R value between the scores of NEI corneal fluorescein staining and the scores computed using the technique described above was equal to 0.8 with statistical significance represented as $p<0.001$. A strong correlation was also found between the NEI score and the intensity obtained with the techniques described above ($R=0.85$; $p<0.001$). Therefore, while following the trend of the NEI scores manually provided by a physician, the grading techniques described herein provides an accurate and high resolution scale that does not rely on human interpretation or arbitrary scoring criteria.

Figure 5A:
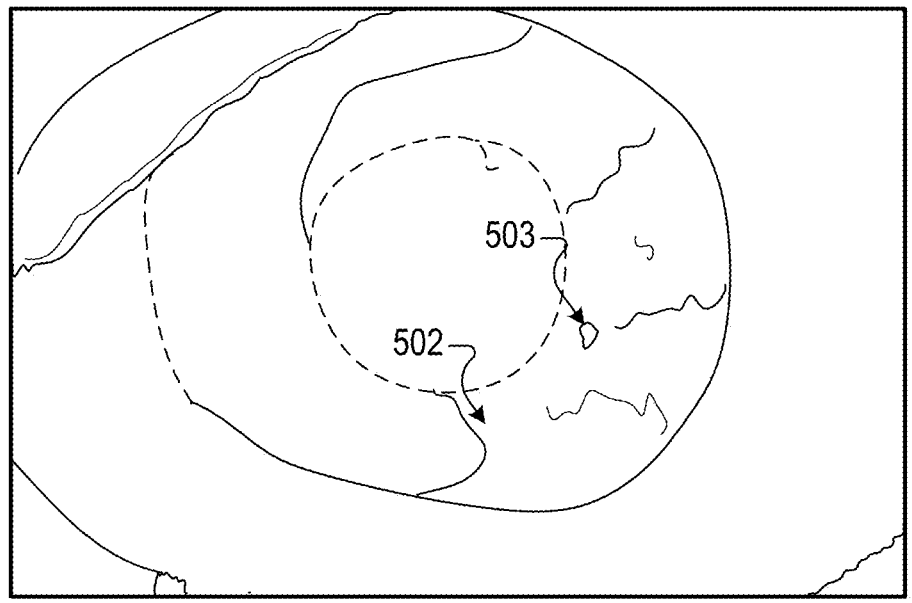
FIGS. 5A-5D is examples of corneal images for which scores have been calculated.
Figure 5B:
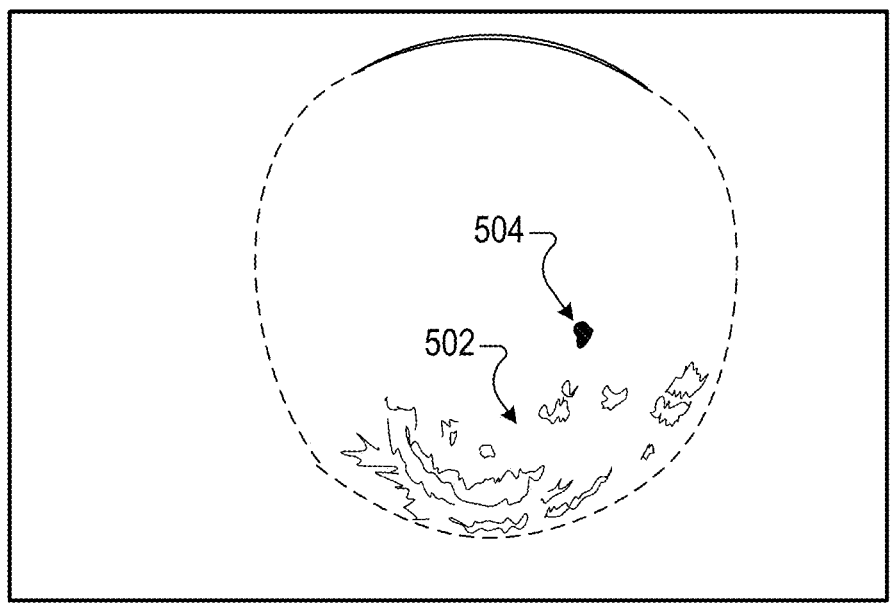

FIG. 5A shows the image of an eye and FIG. 5B shows the corresponding CFS image. The specular reflection 503 in the image of FIG. 5A is represented as the red spot 504 in the CFS image of FIG. 5B. The area including the specular reflection 503 is therefore excluded from the evaluation area. The inferior area 502 of the images in FIGS. 5A and 5B was used as the evaluation area and the image in FIG. 5B scored 84.2 with an average level of fluorescence intensity of 22.

Figure 5C:
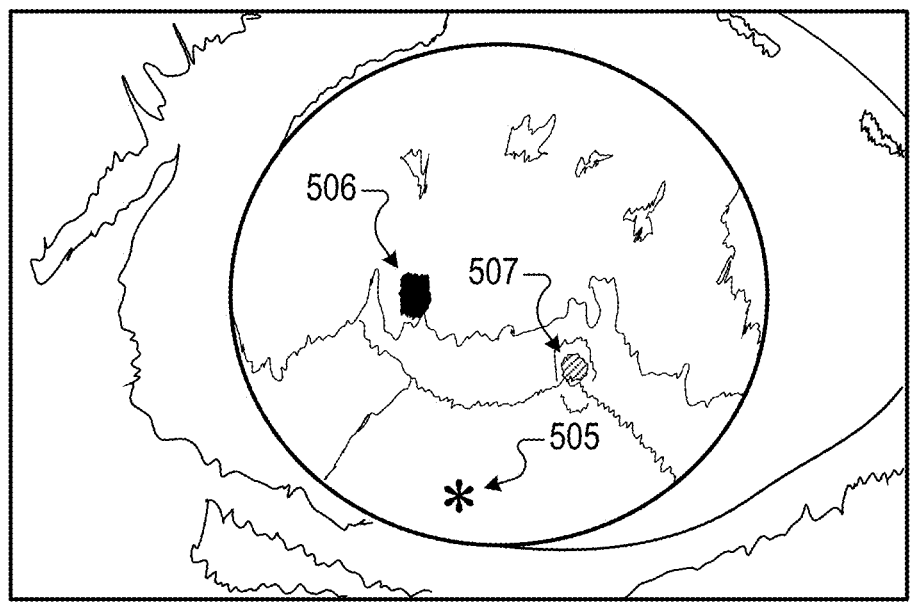
Figure 5D:
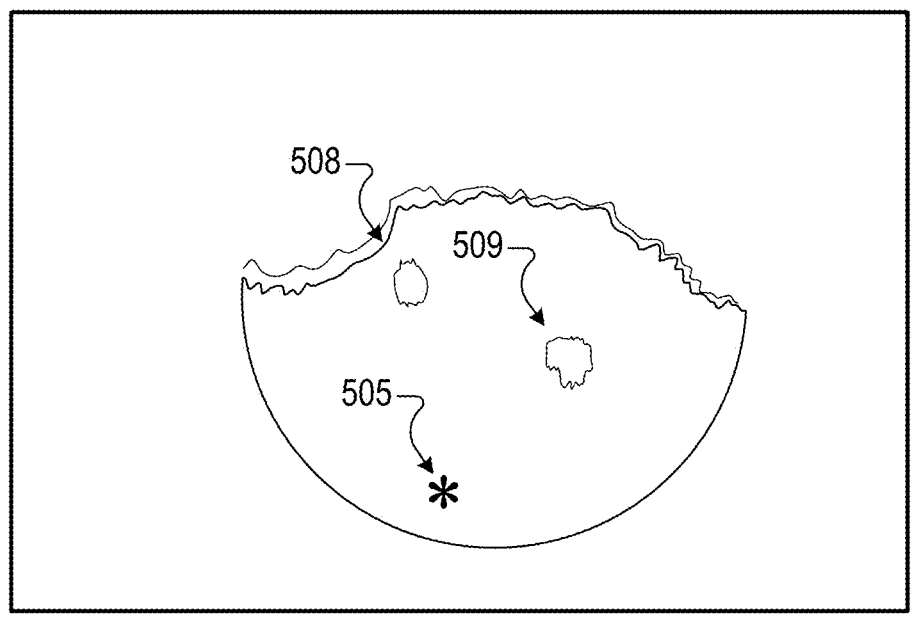

FIG. 5C shows the image of another eye and FIG. 5D shows the corresponding CFS image. The specular reflections 506 and 507 in the image of FIG. 5A are manifested as the spots 508 and 509, respectively in the CFS image of FIG. 5D. The area including the specular reflections 506 and 507 are therefore excluded from the evaluation area. The inferior area 505 of the images in FIGS. 5A and 5B was used as the evaluation area and the image in FIG. 5D scored 100 with an average level of fluorescence intensity of 90.

The algorithm was implemented on the Java-based imaging-processing platform ImageJ (National Institutes of Health; Rasband, ImageJ, U. S. National Institutes of Health, Bethesda, Md., USA (imagej.nih.gov/ij/), 1997-2011; Abramoff et al., Biophotonics International (11)7:36-42 (2004)) as a plug-in.

OTHER EMBODIMENTS

A number of implementations have been described. Nevertheless, it will be understood that various modifications may be made. For example, elements of one or more implementations may be combined, deleted, modified, or supplemented to form further implementations. As yet another example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method for determining a score representing an amount of staining of a cornea, the method comprising:
   obtaining a digital image of the cornea stained with a tracer material;
   processing, by one or more processing devices, the digital image to exclude areas with one or more artifacts, wherein processing the digital image comprises:
   dividing the digital image into a plurality of zones, and
   excluding zones in which a presence of the one or more artifacts are detected to define a plurality of pixels;
   for each pixel of the plurality of pixels:
   determining a plurality of color components that are based on a Cartesian color space,
   determining, from the color components, a hue value in a polar coordinate based color space, and
   determining an amount of staining of the cornea as a function of the hue value; and
   assigning a score to the digital image based on the amount of staining calculated for the plurality of pixels, wherein the score indicates a degree of greenness of the image of the cornea.

2. The method of claim 1, wherein the one or more artifacts include one of a specular reflection and a confocal reflection.

3. The method of claim 1, wherein determining the amount of staining further comprises:
   mapping an angle corresponding to the hue value to a scalar value within a predetermined range; and
   determining the amount of staining as a product of the scalar value and at least one component of the polar coordinate based color space that is different from the hue.

4. The method of claim 1, wherein the tracer material is a fluorophore.

5. The method of claim 4, wherein the fluorophore is fluorescein.

6. The method of claim 5, wherein the digital image is acquired in a presence of blue cobalt light.

7. The method of claim 1, wherein the Cartesian color space is an RGB color space.

8. The method of claim 1, wherein the polar coordinate based color space is an HSV color space.

9. The method of claim 1, wherein the digital images represent corneas afflicted with a corneal epithelial disease.

10. A computer readable storage device having encoded thereon computer readable instructions, which when executed by a processor, cause a processor to perform operations comprising:
    obtaining a digital image of a cornea stained with a tracer material;
    processing the digital image to exclude areas with one or more artifacts, wherein processing the digital image comprises:
    dividing the digital image into a plurality of zones, and
    excluding zones in which a presence of the one or more artifacts are detected to define a plurality of pixels;
    for each of a plurality of pixels:
    determining a plurality of color components that are based on a Cartesian color space,
    determining, from the color components, a hue value in a polar coordinate based color space, and
    determining an amount of staining of the cornea as a function of the hue value; and assigning a score to the digital image based on the amount of staining calculated for the plurality of pixels, wherein the score indicates a degree of greenness of the image of the cornea.

11. The computer readable storage device of claim 10, wherein determining the amount of staining further comprises:
mapping an angle corresponding to the hue value to a scalar value within a predetermined range; and
determining the amount of staining as a product of the scalar value and at least one component of the polar coordinate based color space that is different from the hue.

12. The computer readable storage device of claim 10, wherein the digital images represent corneas afflicted with a corneal epithelial disease.

13. The computer readable storage device of claim 10, wherein the tracer material is a fluorophore.

14. The computer readable storage device of claim 13, wherein the fluorophore is fluorescein.

15. The computer readable storage device of claim 14, wherein the digital image is acquired in a presence of blue cobalt light.

16. The computer readable storage device of claim 10, wherein the Cartesian color space is an RGB color space, and the polar coordinate based color space is an HSV color space.

17. A system for determining a score representing an amount of staining of a cornea, the system comprising:
an imaging system configured to obtain a digital image of the cornea stained with a tracer material; and
a score calculator module configured to:
process the digital image to exclude areas with one or more artifacts, the processing comprising:
dividing the digital image into a plurality of zones, and
excluding zones in which a presence of the one or more artifacts are detected to define a plurality of pixels,
for each of a plurality of pixels:
determining a plurality of color components that are based on a Cartesian color space,
determine, from the color components, a hue value in a polar coordinate based color space, and
determine an amount of staining of the cornea as a function of the hue value, and
assign a score to the digital image based on the amount of staining calculated for the plurality of pixels, wherein the score indicates a degree of greenness of the image of the cornea.

18. The system of claim 17, further comprising a storage device configured to store the score and an association of the score with the digital image.

19. The system of claim 17, wherein the tracer material is a fluorophore that includes fluorescein.

20. The system of claim 17, wherein the imaging system further comprises a light source for radiating blue cobalt light to illuminate the cornea.

* * * * *